United States Patent [19]

Subramanian

[11] Patent Number: 5,292,868
[45] Date of Patent: Mar. 8, 1994

[54] CHELATING AGENTS FOR ATTACHING METAL IONS TO PROTEINS

[75] Inventor: Ramaswamy Subramanian, Frederick, Md.

[73] Assignee: Akzo N.V., Arnhem, Netherlands

[21] Appl. No.: 44,875

[22] Filed: Apr. 8, 1993

Related U.S. Application Data

[63] Continuation of Ser. No. 720,277, Jun. 24, 1991, abandoned, which is a continuation of Ser. No. 438,558, Nov. 17, 1989, abandoned, which is a continuation-in-part of Ser. No. 358,917, May 26, 1989, abandoned.

[51] Int. Cl.$^5$ .................. C07K 15/28; C07K 17/02; A61K 49/02; A61K 39/44
[52] U.S. Cl. .................. 530/391.5; 530/391.1; 530/391.3; 530/391.7; 530/391.9; 530/404; 530/405; 530/408; 530/409; 436/504; 436/545; 436/548
[58] Field of Search .............. 530/391.1, 391.3, 391.5, 530/391.7, 391.9, 404, 405, 408, 409; 424/1.1, 9; 436/545, 548, 504

[56] References Cited

U.S. PATENT DOCUMENTS

| | | | |
|---|---|---|---|
| 4,678,667 | 7/1987 | Meares et al. | 424/1.1 |
| 4,885,363 | 12/1989 | Tweedle et al. | 540/465 |
| 5,057,302 | 10/1991 | Johnson et al. | 424/1.1 |
| 5,204,448 | 4/1973 | Subramanian | 530/391.5 |

FOREIGN PATENT DOCUMENTS 0238196  9/1987  European Pat. Off. .
0296522  12/1988  European Pat. Off. .

OTHER PUBLICATIONS

Lindmo et al. (1984) J. Immunol. Methods 72: 77–89.
Brechbiel et al., Inorganic Chemistry, 25, 1986, pp. 2772–2781.
Subramanian et al., "New Chelating Agent for Attaching Indium-111 to Monoclonal Antibodies: In Vitro and In Vivo Evalution", Bioconjugate Chemistry, (3) 1992.

*Primary Examiner*—Kay K. Kim
*Attorney, Agent, or Firm*—William M. Blackstone

[57] ABSTRACT

A new series of bifunctional chelating agents useful for attaching metal ions to proteins, polypeptides and other polymers and methods for their preparation are described. These reagents are unique in their ability to bind a variety of metal ions and to yield a high metal ion concentration per protein molecule. Using these methods polymeric analogs of these bifunctional chelating agents called Starburst ligands can also be obtained. Protein metal chelates thus obtained will have useful radiophysical, chemical, fluorescent, photochemical and magnetic properties suitable for biomedical applications.

16 Claims, 13 Drawing Sheets

HETA - MoAb CONJUGATES n=1, "a" LiLo1
n=2, "b" LiLo2

DICAP

IDAC

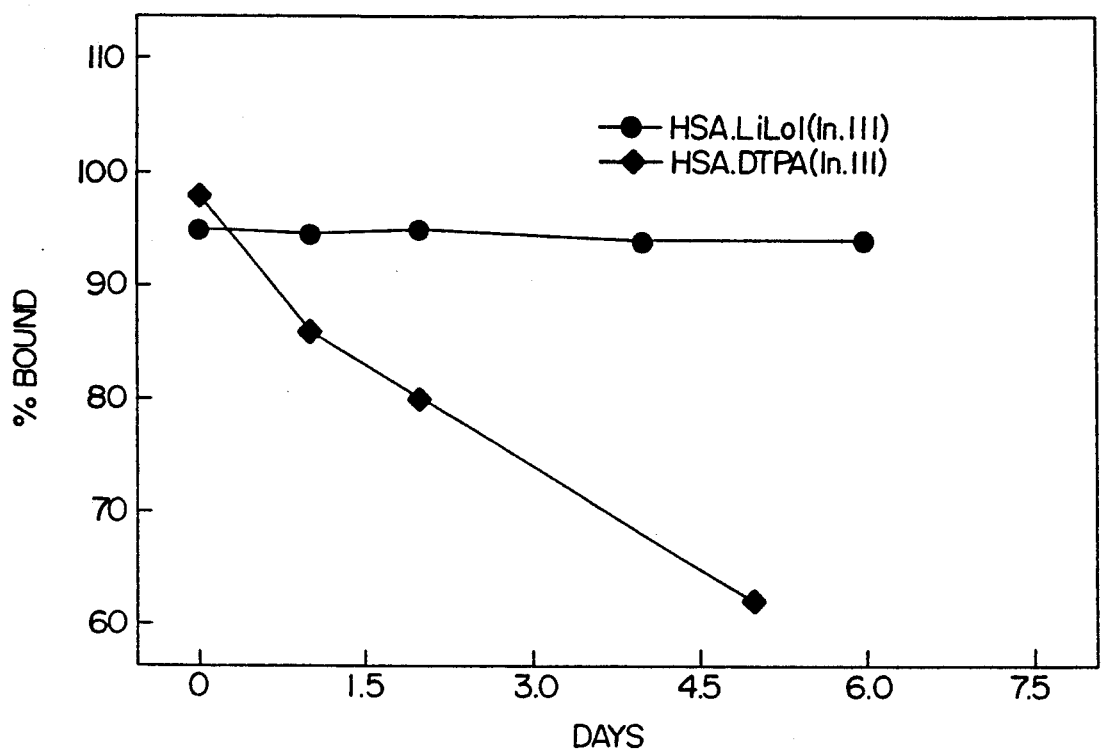
FIG. 3
FIG. 4
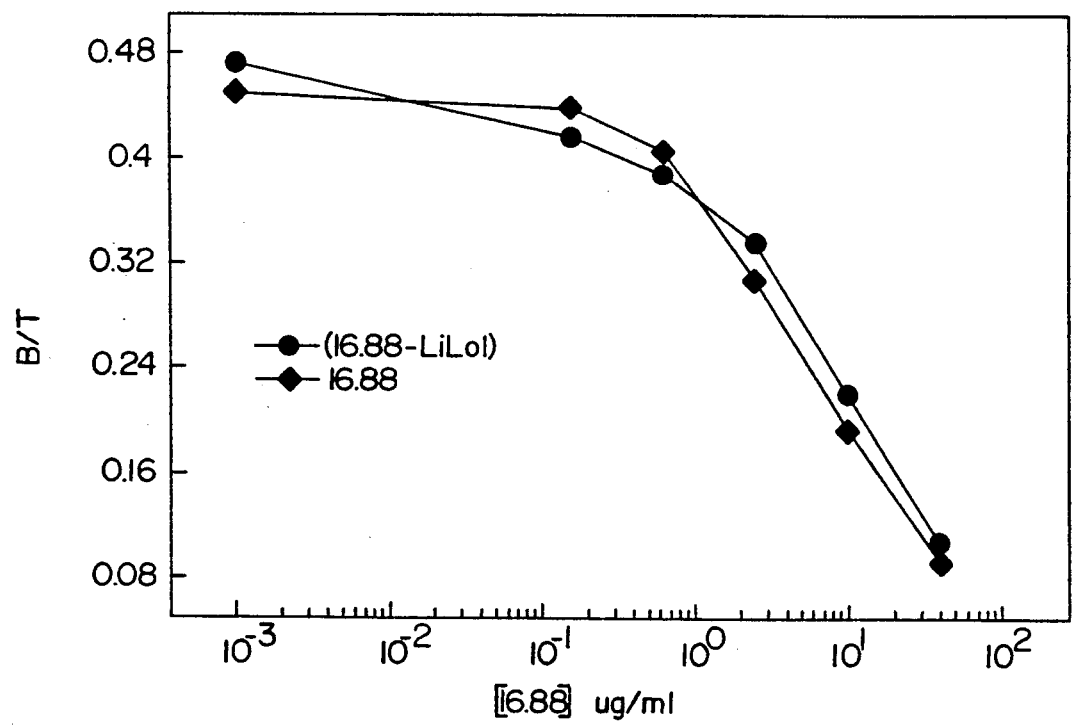

STARBURST LIGANDS

THIN LAYER CHROMATOGRAPHY OF LiLo, HETA AND DTPA
SOLVENT METHYLENE CHLORIDE/METHANOL 93/7(v/v)

FIG. 10

TLC OF In-III LABELED CHELATES

| CHELATE | Rf |
|---------|-----|
| In-DTPA | 0.6 |
| In-HETA | 0.5 |
| In-LiLo | 0.3 |

SOLVENT: 1:1 (volume/volume) MIXTURE OF 10% AMMONIUM ACETATE AND METHANOL

HETA - MoAb CONJUGATES

CHELATING AGENTS FOR ATTACHING METAL IONS TO PROTEINS

This is a continuation of U.S. patent application Ser. No. 07/720,277 filed Jun. 24, 1991, now abandoned, which is a continuation of U.S. patent application Ser. No. 07/438,558, filed Nov. 17, 1989, now abandoned, which is a continuation-in-part of U.S. Ser. No. 07/358,917 filed May 26, 1989, now abandoned.

This invention relates to new chelating agents for attaching metal ions to proteins such as albumin, transferrin, antibodies and etc.

BACKGROUND OF THE INVENTION

Attachment of metal ions to proteins leads to several useful products. These include fluorescent, radioactive and paramagnetic metal ions attached proteins that can be used as probes in vivo in biological systems and in vitro in analytical systems such as radioimmunoassays. For example, attachment of radionuclides to monoclonal antibodies that recognize tumor associated antigens provides radioimmunoconjugates useful for cancer diagnosis and therapy. The monoclonal antibodies are used as carriers of desired substances to specific sites in vivo. Several chelating agents such as diethylenetriaminepentaacetic acid (DTPA), ethylene-diaminetetraacetic acid (EDTA) and macrocyclics have been reported to form stable complexes when attached to protein. However, kinetic instability of the radioimmunoconjugate or the chelate under physiological conditions results in the breakdown of these complexes. Despite several attempts to modify the mode of binding, structure of chelate and etc., in vivo administration of such radioimmunoconjugates results in accumulation of radioactivity in non-target tissues, particularly the liver. Hence, there is an obvious need for new chelating agents for binding radiometals to antibodies forming complexes that do not disassociate when administered to a patient.

SUMMARY OF THE INVENTION

It is an object of this invention to provide a new set of chelating agents for attaching metal ions to proteins and thereby provide an aqueous solution containing antibody-chelate conjugate that is stable in vivo.

It is further an object of this invention to provide a set of chelating agents to bind a variety of metal ions, including In, Y, Gd, Tb, Cu, Co, Sm, Rh, Ru, Re, Tc, Fe, Pb, Ba, actinides, lanthanides and transition metal ions.

It is further an object of this invention to synthesize new chelation structures useful for attaching metal ions to proteins, including monoclonal antibodies.

It is another object of this invention to obtain versatile chelating agents that are not only suitable for binding to low molecular weight proteins such as albumin and IgG, but also to high molecular weight proteins such as IgM ($9 \times 10^5$), lipoproteins ($2 \times 10^6$) and etc.

It is still another object of this invention to obtain an improved method for preparing metal chelate conjugated antibodies.

An additional object of this invention is to obtain chelation structures that provide a high metal ion concentration per antibody molecule without destroying the biological activity of the conjugated protein to a significant extent.

It is still another object of this invention to obtain fluorescent labeled proteins by attaching fluorescent/luminescent metal ions to protein-chelate conjugates.

It is further the object of this invention to obtain metal ion binding reagents that can be attached to chromatographic column materials such as polymers and gels, forming chelate affinity columns.

These and other objects are accomplished by one or more of the embodiments of the present invention.

BRIEF DESCRIPTION OF THE DRAWINGS

The bifunctional chelating agents of the invention are shown in FIG. 1.

FIG. 3 compares the stabilities of Indium-111 labeled HSA-LiLo1 and HSA-DTPA in phosphate buffered saline (PBS), (0.05M, pH 7.2) at 37° C.

FIG. 4 compares the biological activity (immunoreactivity) of a protein-chelate conjugate (LiLo1 conjugated to IgM isotope human monoclonal antibody 16-88) to that of the unconjugated protein (16-88).

FIG. 10 lists the TLC values for In(111) labeled DTPA, HETA and LiLo.

DESCRIPTION OF PREFERRED EMBODIMENTS

Figure 1:
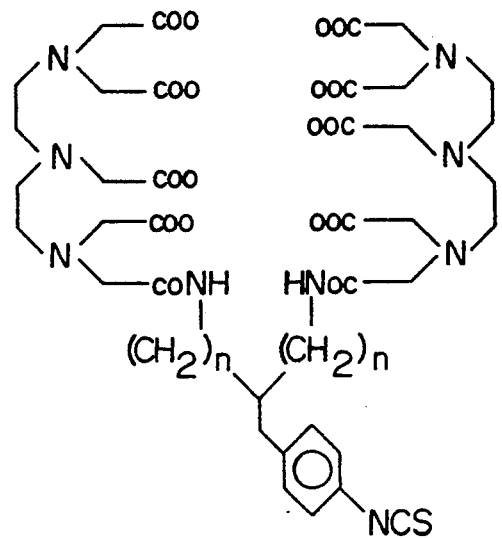
In FIG. 1, "a" is LiLo1, "b" LiLo2, "c" is DICAP, and "d" is IDAC.
Figure 1:
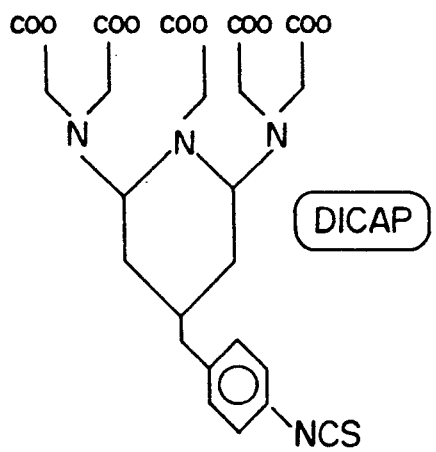
Figure 1:
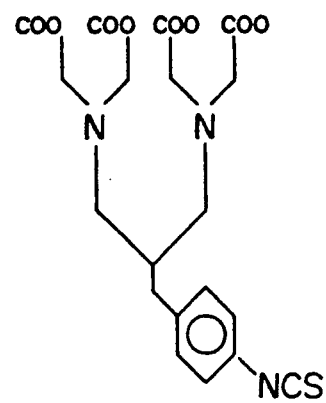

One embodiment of this invention is directed to a buffered solution containing an antibody or protein chelate conjugate wherein all the metal ions are bound to protein via the chelator.

Attachment of radiometals to antibodies requires first the attachment of ligands to antibodies. Ligands, also termed chelators or chelating agents, are compounds that can bind radiometals efficiently through the formation of coordinate bonds. Ligands such as polyaminocarboxylic acids, macrocyclics, crown ethers, cryptands and cyclams can be used to bind radiometals. The choice of the ligand depends on the choice of the radionuclide involved and the properties of the protein conjugated. For radioimmunoimaging and therapy the radionuclides of interest include $^{111}$In, $^{90}$Y, $^{203}$Pb, $^{155}$Sm, $^{212}$Pb, $^{225}$Ac, $^{101}$Rh, $^{97}$Ru, $^{67}$Cu, $^{201}$Tl, $^{99m}$Tc, $^{55}$Co, $^{186}$Re, $^{188}$Re, $^{212}$Bi and $^{213}$Bi. For paramagnetic metal ions, Gd and other similar metal ions can be used. For fluorescence or luminescence based investigations, metal ions such as Tb, Eu, Ru and Rh can be employed.

Ligands suitable for attachment to both proteins and metal ions are often called bifunctional chelating agents. In addition to having a metal binding moiety, these compounds also possess reactive functional groups useful for attachment to proteins. The reactive functional groups are already known in the art. Examples of these groups are isothiocynato, bromoacetamido, diazo, N-hydroxysuccinimide esters and anhydrides. These groups can be incorporated into chelating agents. The metal ions can be part of a linker molecule containing several carbon atoms [$(CH_2)n$] and several other groups. Some of the factors to be considered while constructing an immunoconjugate are: (1) They must be stable, (2) readily bind the metal ions and (3) retain the biological activity of the protein. The chelation structures described in this invention satisfy these conditions.

In addition to the chelating agents, this invention comprises the synthesis of a family of bifunctional chelating agents starting from (p)-nitrobenzyl bromide and diethylmalonate. From the condensed products, several amines such as $(p)NO_2$-Ph-$CH_2$-CH($CH_2NH_2$)$_2$, $(p)NO_2$-Ph-CH($CH_2.CH_2.NH_2$)$_2$ and

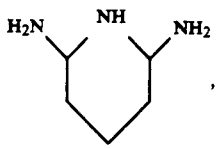

with $(p)NO_2$-Ph-$CH_2$ at C-3 can be prepared. They are the key intermediates from which the metal binding chelating agents a-d in FIG. 1 and HETA in FIG. 8 can be synthesized. These reagents also possess a reactive functional group such as -NCS, -NH-CO-$CH_2$Br, or -$N_2$Br, which can be used to attach them to proteins.

Conventional chelating agents lead to several different products when coupled with proteins (e.g. aggregates). Often use of linkers such as dianhydrides may be the reason for this. By employing linkers such as isothiocyanate or —NH—CO—$CH_2$Br, these complications are avoided.

For preparing the chelates of this invention all reactions were carried out in non-aqueous solvents, such as methanol methylene chloride and THF, and purification was performed by silica gel chromatography. There are several significant aspects to this approach. Using the same sequence of reactions, we have obtained chelates containing carboxyl groups, and/or phenoxyl groups, macrocyclic chelating agents, reagents containing several metal binding groups, and reagents containing a conformationally rigid moiety. These reagents offer a wide variety of metal chelates with unique and useful properties. Further, the sequence of reactions defined can be employed to obtain several other bifunctional reagents, as well as polymeric starburst ligands, such as LiLo (See for example, FIG. 1a).

During the synthesis of LiLo a cyclic byproduct is formed, which is also a useful chelating agent. This cyclic product, 1,12-dicarbonyl, 15-(4-isothiocyanatobenzyl) 1, 4, 7, 10, 13-pentaazacyclohexadecane-N, N', N" triaceticacid, which we refer to as HETA, is a polyaminocarboxylate having three carboxy groups for binding a metal within the cyclic structure. FIGS. 8 through 13 relate to the HETA chelating agent.

Figure 7:
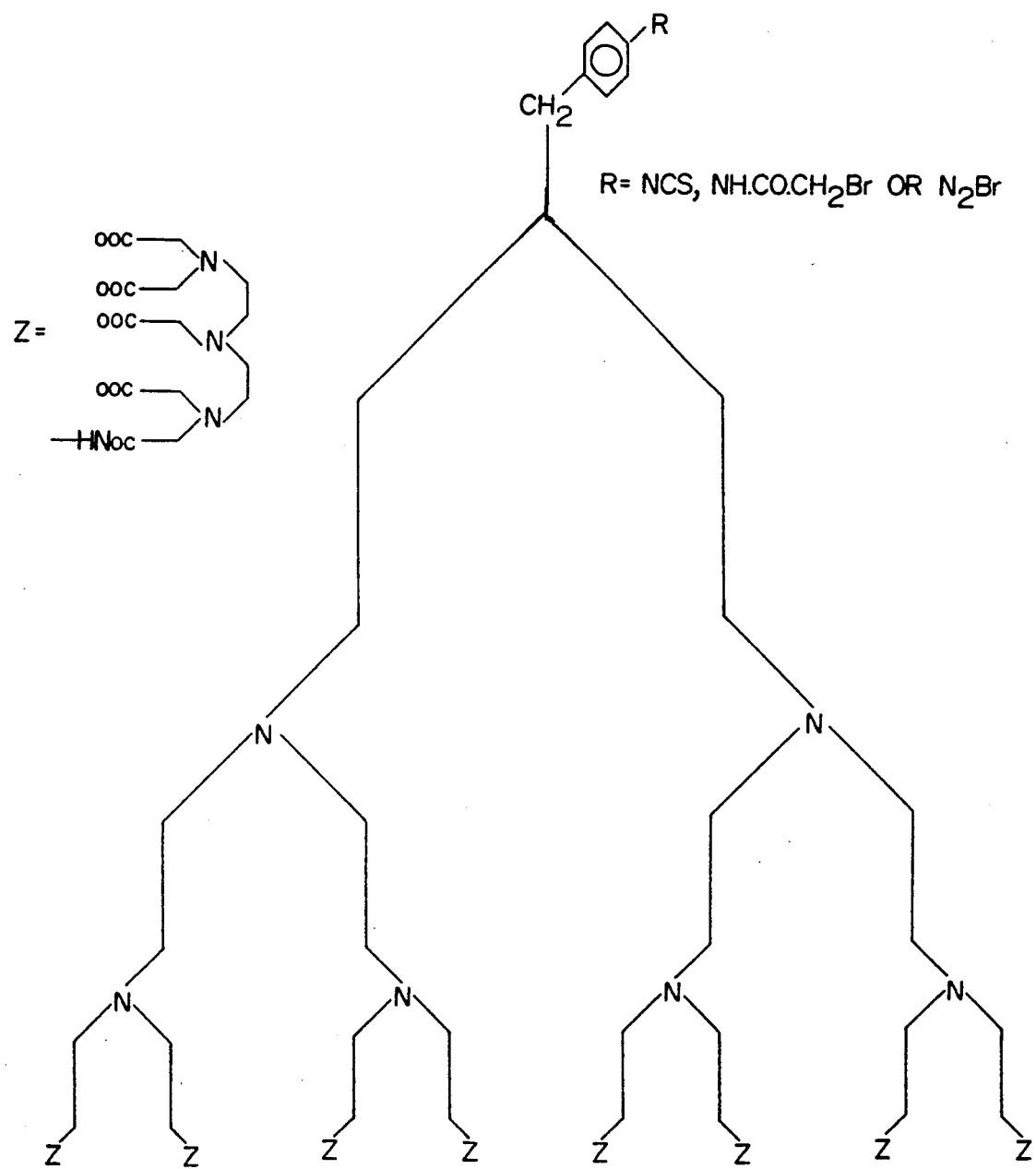
FIG. 7 illustrates a starburst LiLo ligand, in which the binding sites are LiLo type groups, as illustrated in FIG. 1. The number of binding sites can be preselected by design.

Polymeric starburst LiLo ligands, as shown in FIG. 7, are polymeric analogs of IDAC and LiLo. These are molecules obtained by reacting the carboxy methyl ester derivatives (of IDAC, LiLo and etc.) with ammonia, followed by reduction and carboxymethylation.

Figure 6:
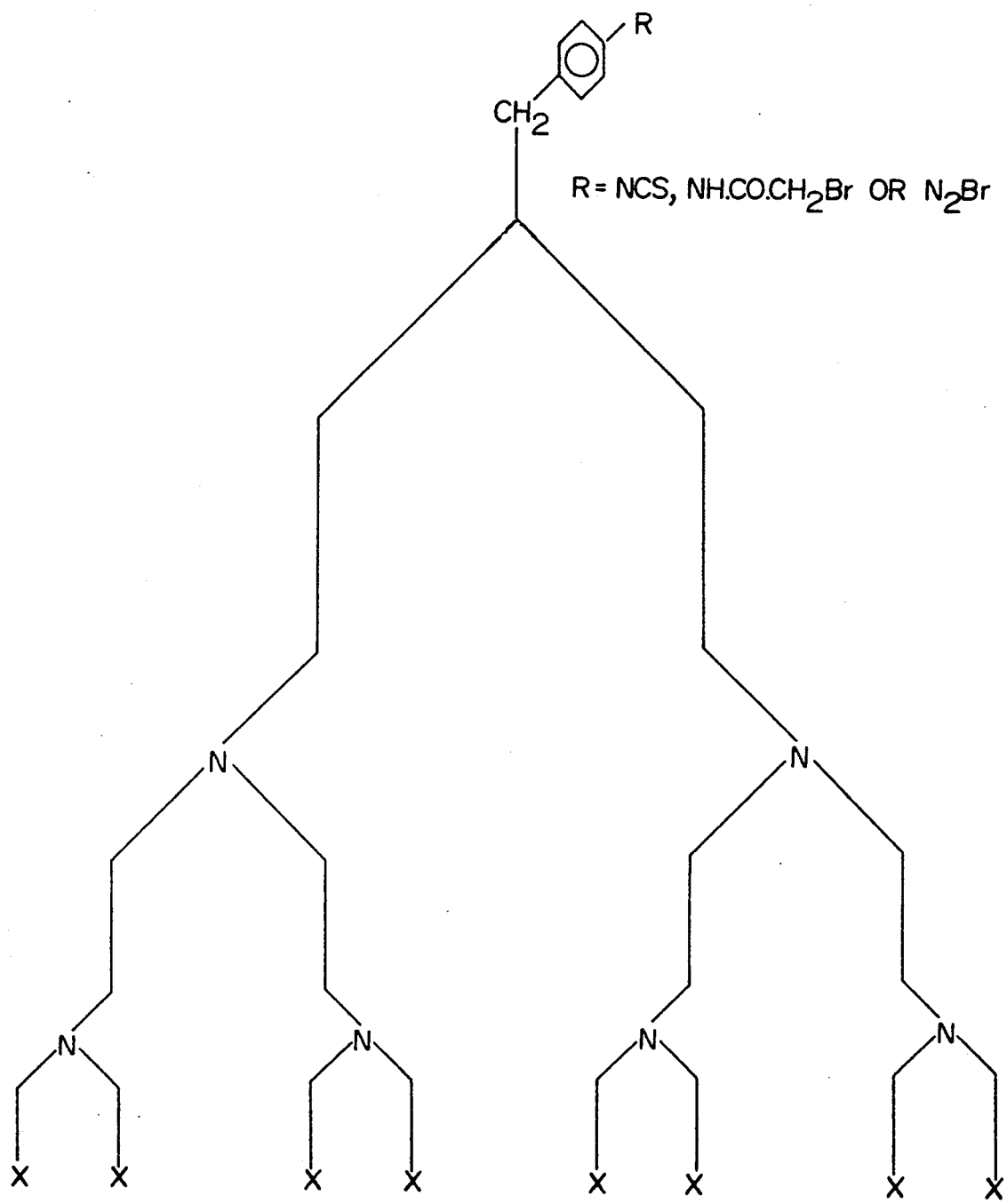
FIG. 6 illustrates a starburst ligand, for which a predetermined number $N[CH_2COO]_2$ binding sites can be incorporated by selection of rows of N.

The process of ammonia reaction, reduction, and carboxymethylation can be continued until a molecule containing the desired number of carboxyl groups is obtained. Instead of ammonia, one can also use ethylene diamine ($NH_2CH_2CH_2NH_2$), propylene diamine ($NH_2$-$CH_2$-$CH_2$-$CH_2$-$NH_2$) diethylene triamine ($NH_2(CH_2CH_2)$-NH-($CH_2CH_2$)-$NH_2$) and so on. Because of their ability to spread in three dimensions as multicarboxyl moieties we have named them 'starburst ligands". This methodology is further adaptable for large scale production of chelates in an automated system, a "multivalent starburst ligand synthesizer," using an instrument similar to a peptide synthesizer that automatically repeats the reaction step a predetermined number of times. Purification of the polymer ligand can be accomplished by gel permeation, silica gel and/or ion-exchange chromatography. The starburst ligand is illustrated in FIG. 6, wherein X is $COO^-$ or $CH_2$-N-Y, in which Y is $CH_2$—$COO^-$ or a further iteration of $CH_2$—N—Y until the desired number of $COO^{13}$ binding sites are available in n rows of N, wherein the number of $COO^-$ groups available for binding equals $2^n$.

Using the above mentioned sequence of reactions, one can obtain a series of reagents useful for attaching different types of metal ions to proteins, e.g. LiLo for $^{111}$In/$^{90}$Y, HETA and IDAC for $^{99m}$Tc, and starburst polymer for Gd, Tb, Eu, and radiometals.

Instead of carboxymethylation of polyamines, one can also condense them with DTPA (using the methods used in the syntheses of LiLol) to obtain a polymer starburst LiLo ligand containing several .N($CH_2COO$)$_2$.$CH_2$.$CH_2$.N($CH_2COO$) $CH_2$.$CH_2$.N ($CH_2COO$).CO.NH— groups. An example of such a ligand is shown in FIG. 7. In FIG. 7, Z is .N($CH_2COO$)$_2$.$CH_2$.$CH_2$.N($CH_2COO$) .$CH_2$.$CH_2$N($CH_2COO$).CO.NH— or —N($CH_2$.$CH_2A$)$_2$, wherein A is the same as Z above or a further iteration of —N($CH_2$.$CH_2A$)$_2$ until the desired number of $COO^-$ binding sites are available in n rows of N, wherein the number of $COO^-$ groups available for binding equals $2^{(n+1)}$.

These reagents can be coupled to proteins by gentle and simple means. One procedure involves incubating the protein and chelating agents in a suitable buffer at pH 6-9 for 1-3 hrs at 37° C., and purifying the protein-chelate conjugate formed by gel filtration chromatography. We coupled these reagents to human serum albumin and the resultant chelate conjugated albumin binds metals such as $^{57}$Co with very high efficiency(>95%). The proteins can be monoclonal or polyclonal antibodies, or other proteins such as transferrin, albumin and derivatives thereof. One can modify the linkers in order to obtain maximum immunoreactivity. The metal ion can be transition metal ions, paramagnetic, radioactive and fluorescent/luminescent metal ions, lanthanides, actinides and others. These include but are not limited to Gd, Tb, Eu, Ru, Rh, Pd, Pb, Sm, Tb, Ga, In, Tl, Fe, Co, Ni, Re, Y, Tc, Cr, Os, Ir, Sb and Cu. The procedure for attaching the metal ions involves incubation of the immunoconjugate with a metal salt solution at pH 5-9, at temperatures of 20°-37° C. for a period of 0.5-6 hrs., or at 4° C. for 24 hours, followed by gel filtration chromatography.

If the metal ion involved is not radioactive, the metal-chelate conjugate can be prepared and purified first, and then attached to the protein to obtain metal-chelate-protein conjugate. Because of the presence of polyaminocarboxylates in the case of LiLo and other higher analogs, one can easily achieve high metal ion concentration. In radioimmunotherapy and magnetic resonance imaging this is of paramount importance, as often the antibody uptake by tumor in patients is <0.005% I.D/g.

Figure 8:
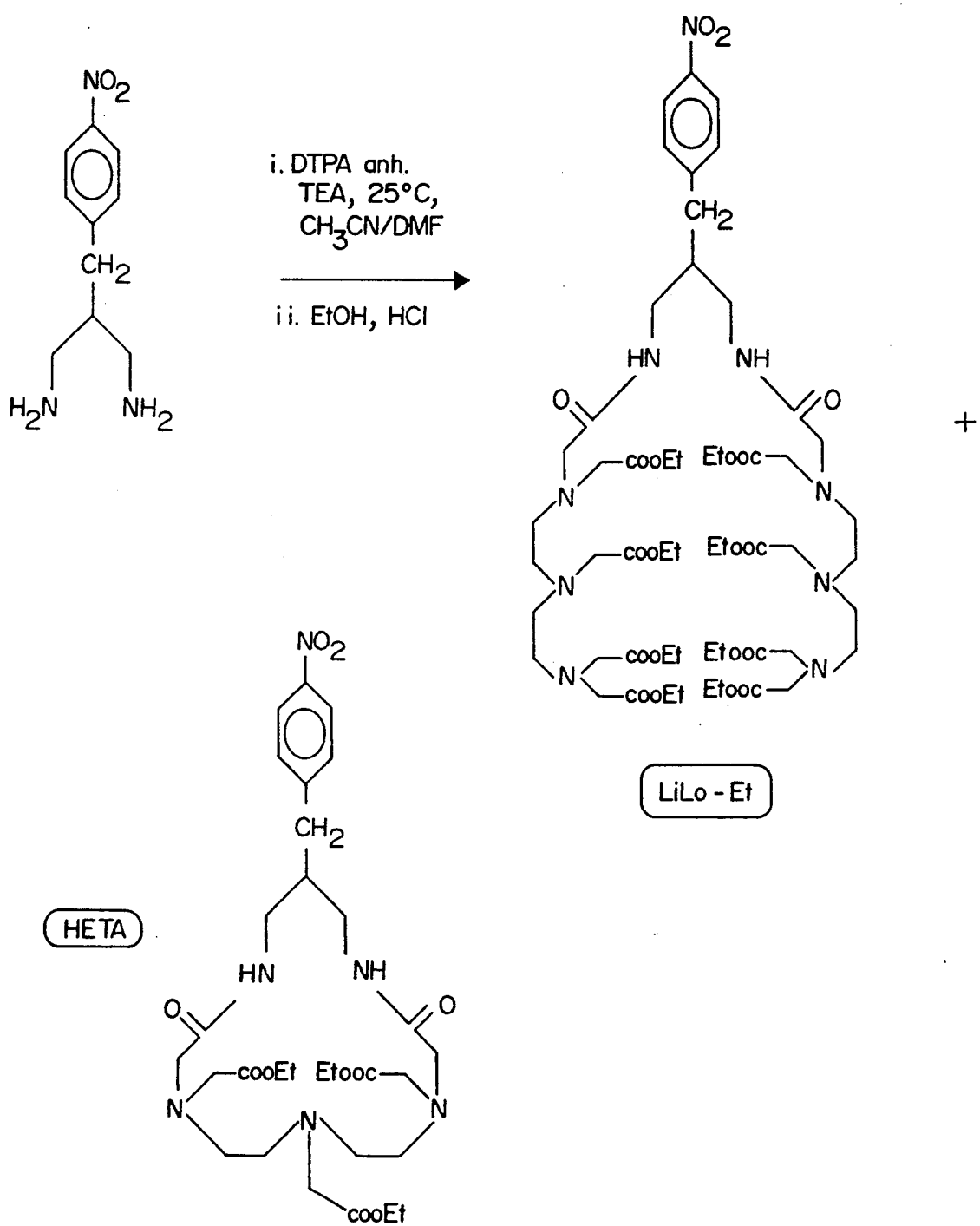
FIG. 8 illustrates the synthesis of LiLo1 and HETA from the diamine. HETA is a byproduct of the production of IX (LiLo) according to the reaction illustrated in FIG. 2B.

All reagents a-d in FIG. 1 and HETA in FIG. 8 are polyaminocarboxylates that will bind radiometals and other metal ions, and can be attached to proteins such as monoclonal antibodies. The choice of the reagent depends on
  a. the application (or the end use)
  b. the nature of metal ion
  c. the protein (biological properties).

For example, when LiLol and IDAC were attached to HSA and labeled with Indium-111, and the rate of decomposition of the radioimmunoconjugate was determined at 37° C. by a DTPA chase technique, it was found that HSA-LiLol-$^{111}$In loses $^{111}$In at the rate of <1%/day, whereas HSA-IDAC-$^{111}$In loses $^{111}$In at the rate of approximately 20% per day. Under similar experimental conditions, HSA-DTPA-$^{111}$In loses $^{111}$In at the rate of 10% per day. These results show that LiLo may be a better chelator for Indium than IDAC and DTPA. However, IDAC can be used for short lived isotopes such as $^{99m}$Tc and $^{55}$Co (half-life approximately 6h.), since in these cases short term stability is more important.

Starburst polymer LiLo ligands will be of use in cases where high metal ion density is required, such as in therapy, in vitro diagnostics (fluorescent metal ions), MRI contrast agents and etc. The significant advantage of usage of starburst ligands is their ability to bind to a large number of metal ions.

The presence of unbound metal ions, if any, in the purified conjugate can be determined using standard analytical techniques such as thin layer chromatography (ascending), NMR, IR, or visible or fluorescence spectroscopy.

EXAMPLE I

Conjugation and Stability Studies

For stability studies, HSA-IDAC or HSA-LiLo conjugate was first prepared by reacting HSA (30 mg/ml, 0.05M PBS solution, pH7.2) with LiLo or IDAC (HSA: LiLo/IDAC molar ratio 1:10) at 37° C. for 2 hours. Unbound chelate was removed by gel filtration chromatography (G-50 Sephadex, Pharmacia). The conjugate (HSA-LiLo, HSA-IDAC) was collected and the concentration of the protein determined by absorption at 280 nm. The preparation of HSA-DTPA involved the addition of DTPA dianhydride to HSA in PBS buffer (0.05M, pH7.2) and incubation at room temperature for 15 min. Unbound chelate was removed by gel filtration chromatography as described above.

The conjugate was labeled with In-111 in a buffer (0.05M citrate/0.5 M acetate, pH 5.5) DTPA was added to bind any unbound Indium-111, and the labelled conjugate was purified by G-50 or G-25 gel filtration chromatography. The purity of the immunoconjugate was determined by ITLC in PBS buffer using Gelman ITLC-SG chromatography paper.

Stability studies were carried out in 0.05M PBS buffer pH 7.2 at 37° C. At periodic intervals an aliquot of the solution was removed and treated with excess DTPA solution to chelate any dissociated $^{111}$In. Thin layer chromatography analysis using ITLC-SG strip (Gelman Sciences) in PBS buffer (0.05M, pH 7.2) was carried out, and the ITLC strip was cut into two pieces, and the indium (111) activity was determined using a gamma counter.

$$100 \times \frac{\text{radioactivity at the bottom strip}}{\text{radioactivity at the (bottom + top) strips}}$$

equals the percentage of $^{111}$In bound to protein.

Results obtained with $^{111}$In-HSA-LiLo and $^{111}$In-HSA-DTPA are shown in FIG. 3.

The chelators LiLo and IDAC were also conjugated to a human monoclonal antibody 16.88. Human monoclonal antibody 16.88 is an IgM isotype produced by a spontaneously transformed human lymphoblastoid cell line, obtained from the peripheral blood lymphocytes of colon carcinoma patients, which expresses the Epstein—Barr nuclear antigen. Attaching radiometals to IgM monoclonals has been reported to be difficult when compared with IgG's or other proteins. Conventional chelating agents such as DTPA anhydrides lead to aggregation of the antibody; in addition, the recovery of the radiolabeled MoAb is low. Such a low recovery was not observed in the cases of radiolabeled 1688-LiLo, 1688-IDAC and 1688-HETA.

The new chelating agents such as IDAC and LiLo were conjugated to 16.88. By a competitive binding assay, the immunoactivity of these conjugates in comparison with unconjugated 16.88 was determined. In this assay antigen was coated on a microtiter plate and treated with 16.88 labeled with radioiodine. This was then allowed to compete with unconjugated 16.88 or 16.88-LiLo and 16.88-IDAC. Results obtained by this assay show that both 16.88-LiLo and 16.88-IDAC were as immunoreactive as unconjugated 16.88. Results obtained with 16-88 are shown in FIG. 4.

The number of chelates per MoAb was determined by known methods in the state of the art. In general, this method involved the addition of known amounts of InCl$_3$ containing $^{111}$InCl$_3$ to the immunoconjugate, and incubating the mixture in 0.05M citrate/0.5M acetate buffer, pH 5.5, for 30 min. at room temperature (23°-27° C.) This was followed by the addition of excess DTPA solution to chelate the unbound Indium. After 5 minutes, an aliquot of the mixture was spotted on TLC (thin layer chromatography). Chromatography was carried out using 10% ammonium acetate (aqueous) and methanol (1:1 by volume) as the eluant mixture. $^{111}$In labeled protein stays at the origin whereas In-DTPA moves (Rf=0.6). By cutting and counting the various portions of TLC, one could determine the number of chelates per protein, since the concentrations of protein and Indium taken in the reaction mixture are known. Normally this ratio was 1-5.

Figure 5:
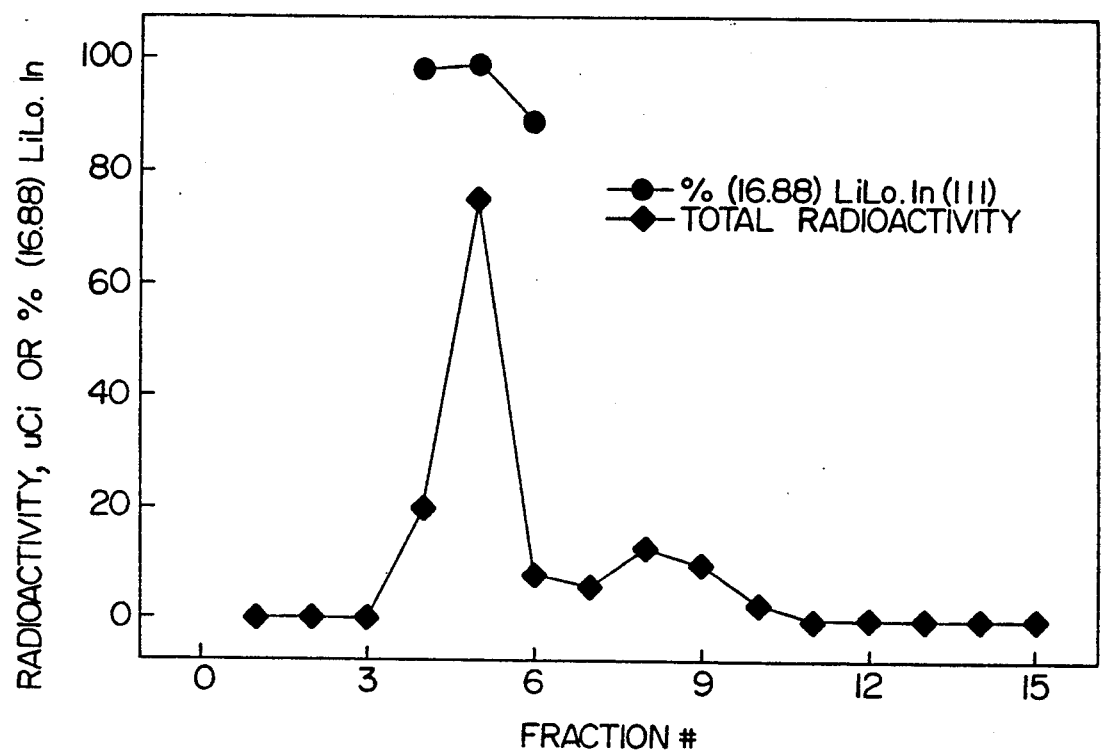
FIG. 5 illustrates the purification of (16.88)LiLo$^{111}$In by gel filtration chromatography.

The immunoreactivity of these conjugates was also determined by a direct cell binding assay as suggested by Lindmo, T. et al. *J. Immunol.Meth*, 72(1), 77-79(1984). In this assay 16.88 - chelate conjugates were labeled with $^{111}$In and purified by gel filtration chromatography. FIG. 5 describes the purification of (16.88)LiLo$^{111}$In by gel filtration (Sephadex, G-25) chromatography. The first peak (fractions #3-#6, 0.9 ml/fraction) contains the radioimmuno conjugates. PBS buffer (0.05M, pH 72) was used as the eluant. The labeled conjugates were incubated with either WiDr cell lines or the antigen, and the percentage of activity bound to the cells or antigen was determined. In both cases of 16.88−LiLo−$^{111}$In and 16.88−IDAC−$^{111}$In the immunoreactivity was >95%.

These results confirm the chelators IDAC and LiLo can be used to attach $^{111}$In to the human monoclonal antibody 16.88 with no significant loss of immunoactivity.

As observed in the case of HSA-chelator conjugates, 16.88−LiLo−$^{111}$In was much more stable in PBS buffer solution (<1% per day) than 16.88 - IDAC $^{111}$In (>10% per day) under physiological conditions. However for short-lived isotopes like $^{99m}$Tc, 16.88 - IDAC may be a good candidate. For $^{90}$Y, which has properties similar to that of indium, 16.88−LiLo will be a good conjugate for in vivo applications.

EXAMPLE II

Synthesis of DICAP

Figure 2A:
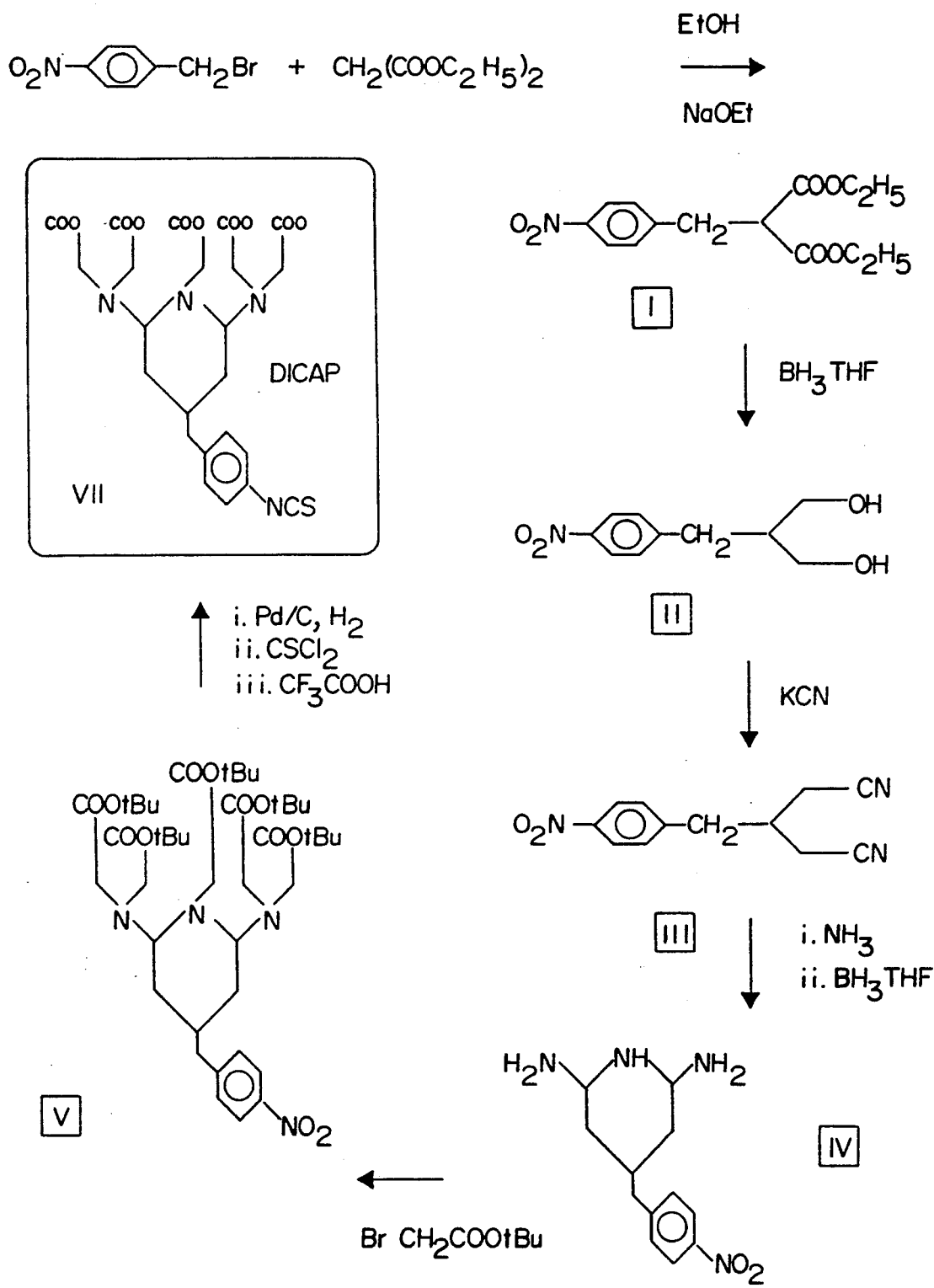
FIGS. 2A and B illustrate synthetic procedures for obtaining metal-binding chelating agents, DICAP, IDAC and LiLo.
Figure 2B:
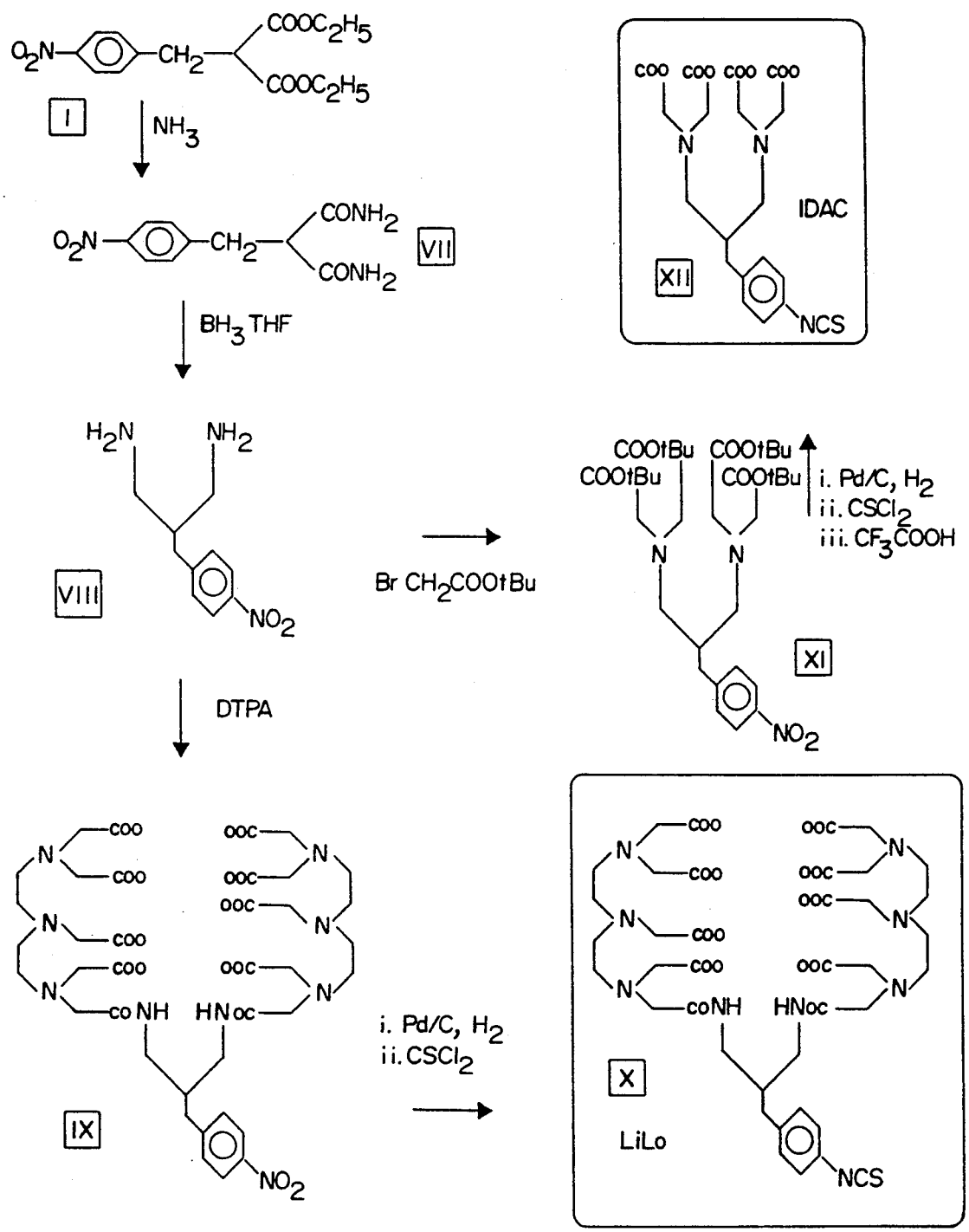

The synthesis of LiLo, DICAP and IDAC is described in FIG. 2. P-nitrobenzylbromide was condensed with diethyl malonate to obtain p-nitrobenzyl diethylmalonate, which was reduced to a diol, converted to a dinitrile and then converted to a triamine. Carboxymethylation followed by reduction and treatment with CSCl$_2$ and CF$_3$COOH yielded DICAP.

p-nitrobenzyl diethylmalonate was directly reduced to a diamine, and condensed with DTPA to obtain LiLo 1. This condensation was carried out in three different ways.

1. Condensation between the diamine and DTPA methyl ester.
2. Coupling between the diamine and DTPA cyclic anhydride.
3. A reaction between the diamine and DTPA acid by the mixed anhydride method.

In our experiments with paths 2 and 3, the product obtained was converted to a methyl ester, purified by silica gel chromatography and converted to LiLo 1. Reduction of dinitrile (III) to a diamine, followed by carboxymethylation, reduction with hydrogen in the presence of Palladium on activated carbon, and treatment with CSCl$_2$ and trifluoroacetic acid yielded LiLo2.

Carboxymethylation of the diamine followed by reduction and treatment with CSCl$_2$ and CF$_3$COOH yielded IDAC. Details of the synthesis are give below:

A. 2(4-nitrobenzyl)diethylmalonate(I)

6.9 g (0.3 m) of sodium metal was added gradually to a stirred solution of 300 ml absolute ethanol under a nitrogen atmosphere. After all metal had dissolved 96 g (0.6 m) diethylmalonate was slowly added dropwise to the solution. This was followed by the addition of 65 g (0.3 m) of 4-nitrobenzylbromide in portions over one hour. The solution was heated to reflux for 24hrs., and precipitated byproduct was filtered off. The solution was evaporated and the crystallized product was filtered and washed with ethanol. Yield 34.9 g(40%),m.pt.60° C. Ir 1736cm$^{-1}$, 1524 cm$^{-1}$, 1346 cm$^{-1}$, 1151 cm$^{-1}$, 852cm$^{-1}$, KBr pellet. NMR, CDCl3, 8.14 d, 2H; 7.37 d, 4.15, 9, 4H; 3.64,t 1H; 3.30,d.2H; 1.22,t,6H.

B. 2-(4-nitrobenzyl)-1,3-propanediol (II)

11.3 g (0.038 m) (I) was dissolved in 20 ml anhydrous THF and injected into a stirred solution of 190 ml 1M BH$_3$-THF solution under a nitrogen atmosphere at 4° C. The solution was slowly heated to reflux for 18 hours. The solution was then cooled to room temperature and methanol was added in small portions to quench the excess BH$_3$ complex. The solution was then rotoevaporated. Further purification was performed by silica gel chromatography. Yield was 6.3 g (78%), mpt. 85° C. IR(KBr pellet) 3260 cm$^{-1}$, 1539 cm$^{-1}$, 1351 cm$^{-1}$, 1030 cm$^{-1}$. NMR 3.73 ppm, d,4H; 2.78 ppm, d, 2H; 2.35 ppm,s,2H; 2.03 ppm,s,1H.

C. 3-(4-nitrobenzyl)1,5-pentanedinitrile(III)

6.9 g(0.036 m)p-toluenesulfonylchloride (tosyl) was dissolved in 10 ml dry pyridine and cooled to 4° C. 2.5 g (0.012 m) II was diluted in 5 ml dry pyridine and added slowly to the stirred tosyl solution with cooling. The solution was stirred for 15 min. at 4° C., then allowed to warm to room temperature and stirred for 3 hrs. The reaction was quenched by pouring the solution slowly with stirring into 100 ml of 30% HCl at 4° C. The product was extracted with CH$_2$Cl$_2$, evaporated and crystallized in ethanol to produce the tosyl derivative. mpt 85-89C. IR(KBr pellet) 1524 cm$^{-1}$, 1352 cm$^{-1}$, 1194 cm$^{-1}$, 1176 cm$^{-1}$.

3.1 g KCN was suspended in a stirred solution of 30 ml absolute ethanol at 4° C. The above tosyl derivative was dissolved in a 1:1 mixture of CH$_2$Cl$_2$:EtOH and added to the KCN mixture. The solution was slowly heated to reflux for 24 hours. The solution was then rotoevaporated, extracted with CH$_2$Cl$_2$, filtered and evaporated. The oil was then run down a silica gel column to be isolated as an orange oil (III). 1.9 g Yield 70%, IR (NaCl plate) 2248 cm$^{-1}$, NMR 2.96 ppm,s,2H; 2.5 ppm,s,4H; 2.13 ppm,m,1H.

D. (4-nitrobenzyl)glutarimidine(IV)

2.2 g (0.0096m) III was dissolved in 100 ml dry methanol. Ammonia gas was bubbled through the solution to saturation. The solution was added to a pressure reactor (bomb), sealed and heated at a pressure of 80-100 psi for 15 hrs. The bomb was cooled to ambient temperature, the reaction mixture removed and the solvent evaporated to a thick dark oil. IR (NaCl plates) 1666 cm$^{-1}$.

The above product was dissolved in 25 ml of anhydrous THF (tetrahydrofuran) and added to 75 ml 1M BH3.THF (borane tetrahydrofuran) solution at 4° C. under a nitrogen atmosphere. The solution was then allowed to warm to room temperature and stirred at 25° C. for 4 days. Thereafter, the reaction was quenched with methanol and the solution concentrated by evaporation. The oil was dissolved in CH$_2$Cl$_2$ and HCl gas was bubbled through the solution to precipitate the product. IR (KBr pellet) 1604 cm$^{-1}$, 3418 cm$^{-1}$. The product was fluorescamine positive showing the presence of a primary amine. It also yielded a positive test for a secondary amine.

E. 2,6-diamino-4-(4-nitrobenzyl)-1-azacyclohexyl-N,N',N', N'',N''- pentaacetic acid tert-butyl ester (V)

54 mg (IV) was dissolved in 3 ml dry methanol. Triethylamine was added, followed by 250 μl of tert-butyl bromoacetate. The solution was evaporated to dryness and then run down a silica gel column with CH$_2$Cl$_2$ and a gradient increase in methanol content. Yield 25%. NMR showed ratios of benzyl H's to t-butylH's 4:44.2 (calculated 4:45); tertbutyl H's 1.47 ppm, 3 distinct esters ratio 2:2:1; carboxymethyl H's 3.40 ppm, 9.6 H's (theoretical-10).

F. DICAP (VI)

15 mg (V) was dissolved in 5 ml methanol and cooled to 4° C. A catalytic amount of 10% palladium-carbon was added with stirring. $H_2$ gas was then bubbled through the stirred reaction mixture at 4° C. After 10 min the solution was warmed to 25° C. and hydrogen addition was continued for an additional 12 hrs. The solution was then filtered to remove the catalyst. The product tested positive for primary amine by a fluorsescamine assay.

The above solution was stirred at 25° C. with the slow addition of 0.1 ml thiophosgene (5 hrs). The solution was then evaporated to an orange sticky film. IR (KBr pellet) showed NCS peak at 2106 $cm^{-1}$. The tert butyl esters were hydrolyzed and evaporated to dryness.

EXAMPLE III

Synthesis of LiLol

A. 3-(4-nitrobenzyl)diamidomalonate(VII)

4.3 g (I) was dissolved in 150 ml of methanol, cooled to 4° C., and ammonia was bubbled through the solution to the point of saturation. The solution was stoppered and kept at 4° C. for 48 hrs. The precipitated product was filtered and rinsed with methanol. IR (KBr pellet) 3441 $cm^{-1}$, 3392 $cm^{-1}$, 1678 $cm^{-1}$, 1657 $cm^{-1}$.

B. 2-(4-nitrobenzyl)1,3-diaminopropane (VIII) Dihydrochloride Salt 2.0 g (VII) was suspended in THF (tetrahydrofuran) (20 ml) and added to a stirred 60 ml 1m $BH_3$.THF solution at 4° C. The reaction was slowly heated to reflux for 15 hrs. The solution was quenched with methanol and HCl bubbled through with no external cooling until product separated as a yellow oil. The solid was filtered and rinsed with methanol. Yield 2.17 g (91%), IR (KBr pellet) 2934 $cm^{-1}$, 1600 $cm^{-1}$, 1514 $cm^{-1}$ 1353 $cm^{-1}$.

C. Nitro "LiLo" Methyl Ester (IX)

300 mg (VIII) and 3.3 g DTPA pentamethyl ester were dissolved in 10 ml dry methanol and heated to reflux for 7 days. The reaction mixture was evaporated and purified by silica gel column chromatography. The product was fluorescamine negative. Yield 17.5%. IR (KBr pellet) 1741 $cm^{-1}$, 1654 $cm^{-1}$, 1348 $cm^{-1}$, 1204 $cm^{-1}$.

D. ICN-LiLo-Methyl ester(X)

The nitro group was converted to amino and then to isothiocyanato groups by the procedure employed for DICAP, as described above. Synthesis of LiLol:

LiLo-methyl ester (1X) was also obtained by a mixed anhydride method.

1.0 g (0.0025M) DTPA was suspended in 30 ml $CH_2Cl_2$ with 2 ml triethylamine under $N_2$ ATM. The solution was stirred for 24 hours at 25° C., then cooled to approximately −10° C. in an ice/salt bath. 250 ml (0.0025M) ethyl chloroformate was added to the solution dropwise. The solution was stirred for 25 min., 367 mg VIII (0.00125M) was dissolved in 5 ml $CH_2Cl_2$ with 0.5 ml triethylamine, and cooled to −5° C. This was added to the mixed anhydride solution dropwise with strong stirring. The solution was kept below 0° C. for 2 hours, then slowly allowed to warm to room temperature and let stir overnight. The solution was then evaporated and the residue dissolved in dry $CH_3OH$ (50 ml), 4 ml thionyl chloride was added dropwise under $N_2$ ATM. The solution was then heated to reflux for 5 hours. The volatiles were evaporated and the residue run down a silica column ($CH_2Cl_2$ with $CH_3OH$ gradient). IR (KBr Pellet) 1742 $cm^{-1}$, 1664 $cm^{-1}$, 1520 $cm^{-1}$, 1347 $cm^{-1}$, 1207 $cm^{-1}$.

Synthesis of IDAC-$NO_2$(XI)

500 mg VIII (0.00177M) was dissolved in 10 ml $CH_3OH$ and 2 ml triethylamine. 2.0 ml t-butylbromoacetate was added. The solution was stoppered and left to react at 25° C. for 7 days, keeping the solution basic with triethylamine. The solution was evaporated and the residue run down a silica column ($CH_2Cl_2$, $CH_3OH$ gradient). The product was a light yellow oil 818 mg (69%) IR (KBr Pellet) 1736 $cm^{-1}$, 1522 $cm^{-1}$, 1368 $cm^{-1}$, 1345 $cm^{-1}$, 1149 $cm^{-1}$. IDAC-ICN(XII) was prepared by similar steps used to prepare DICAP-ICN.

EXAMPLE IV

LiLol was also be prepared by an alternate method using DTPA dianhydride. 20 mg (VIII) was dissolved in 10ml water. 105 mg DTPA dianhydride was added and the solution shaken until dissolved. This was maintained at 4° C. for 5 days, then reduced immediately. A catalytic amount of 10% Pd/C was added and hydrogen was bubbled through the solution for 6 hrs. at room temperature, then stirred under a hydrogen atmosphere overnight. The solution was filtered, converted to isothiocyante using thiophosgene, and the excess thiophosgene extracted with ether. IR spectrum showed a peak at 2126 $cm^{-1}$, characteristic of isothiocyanate.

EXAMPLE V

DICAP (VI) was also prepared by an alternate method. 200 mg (IV) was dissolved in 1 ml water with the addition of 1N NaOH solution to make it basic. 680 mg bromoacetic acid was (pH>8) added gradually and the solution was maintained at 37° C. for 3 days. The solution was negative to a fluorescamine assay. The solution was concentrated and was run down an AG1x8 anion exchange column using a gradient elution of 1M to 7M formic acid The fractions (3 ml) were lyophilized. The DICAP eluted from fractions 271-304. IR (KBr pellet) 3424 $cm^{-1}$, 2934 $cm^{-1}$, 1736 $cm^{-1}$, 1233 $cm^{-1}$, 1063 $cm^{-1}$.

The examples are presented only for the purpose of illustration and not to limit the invention. Further, the proteins, antibodies, radionuclides and metals described above are offered only as examples. The invention is intended to encompass conjugation with any peptides, proteins or polymers and any radionuclides or any metals within the full scope of the appended claims.

EXAMPLE VI

Synthesis of HETA

The cyclic byproduct HETA is formed during the production of LiLo, as illustrated in FIG. 8. Under the reaction conditions set forth below approximately 15% of the product is HETA, which can be separated by silica gel column chromatography.

6.8 g diethylenetriamine pentaacetic acid dianhydride was suspended in 20 ml methylene chloride and 10 ml triethylamine. 900 mg of the diamine was dissolved in 5 ml methylene chloride and added to the solution with strong stirring. This was stirred at room temperature for 2 days. The solvent was then evaporated. A solution of 10 ml thionyl chloride in 100 ml absolute ethanol was added to the reaction mixture under a nitrogen atmosphere. It was then refluxed for 5 hours. The solvent was evaporated and the resulting product dissolved in 5M NaOH solution and quickly extracted with methylene chloride. The organic layer was dried with magnesium sulfate, decanted, and evaporated. The resulting oil was run down a silica gel column (3% methanol in methylene chloride). Yield of HETA was 1.3 g.

Figure 9:
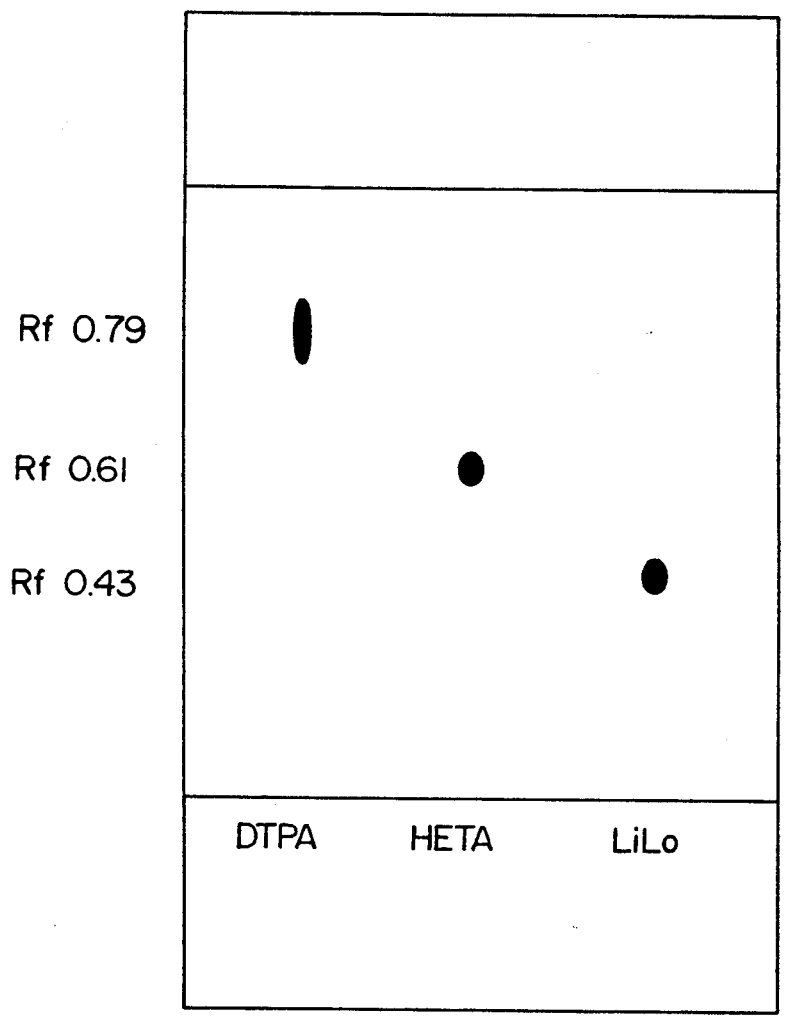
FIG. 9 shows the TLC of DTPA, HETA and LiLo ethyl esters.
Figure 11:
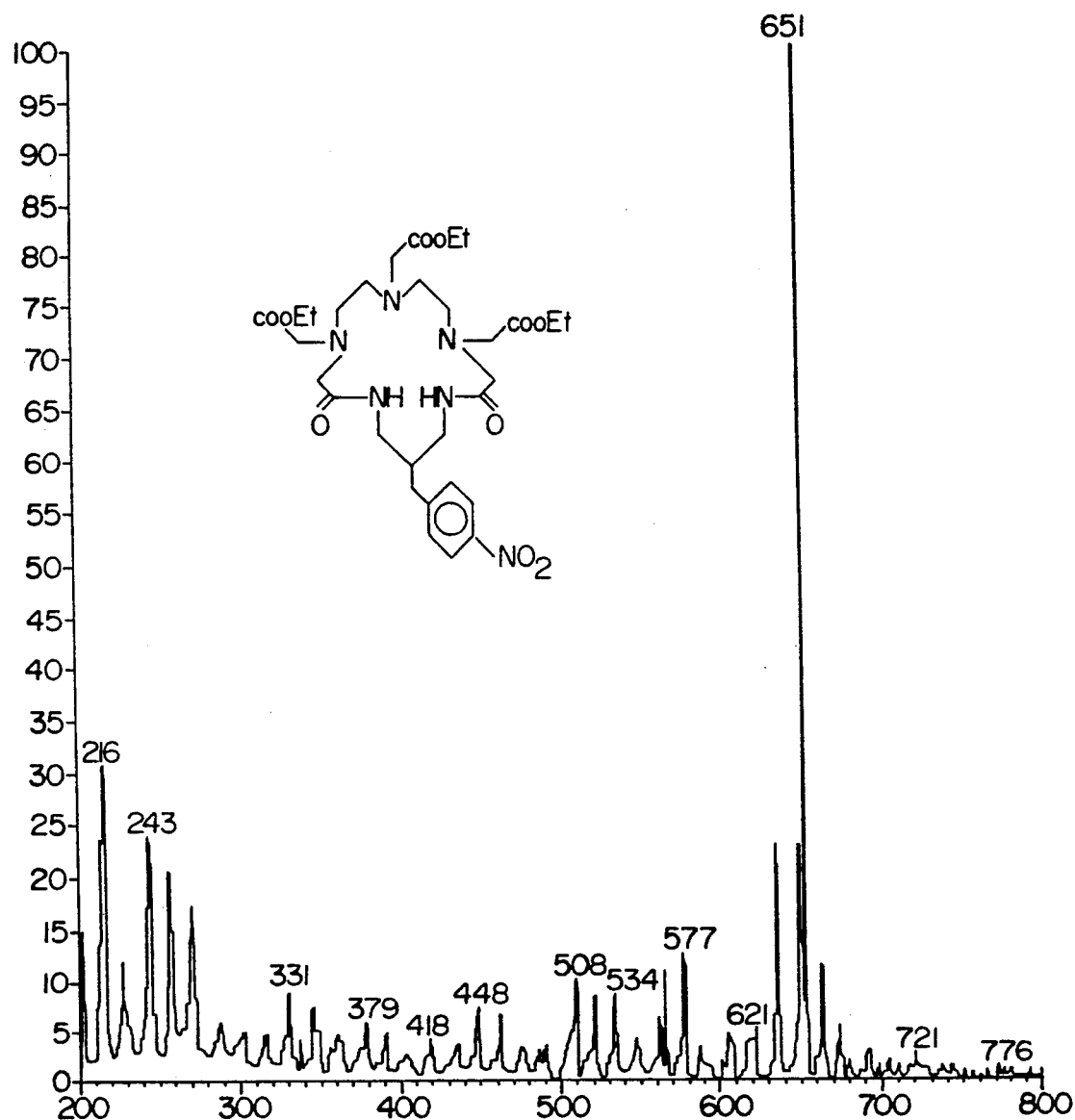
FIG. 11 reports the FAB Mass Spectral data for nitro-HETA ethyl ester.
Figure 12:
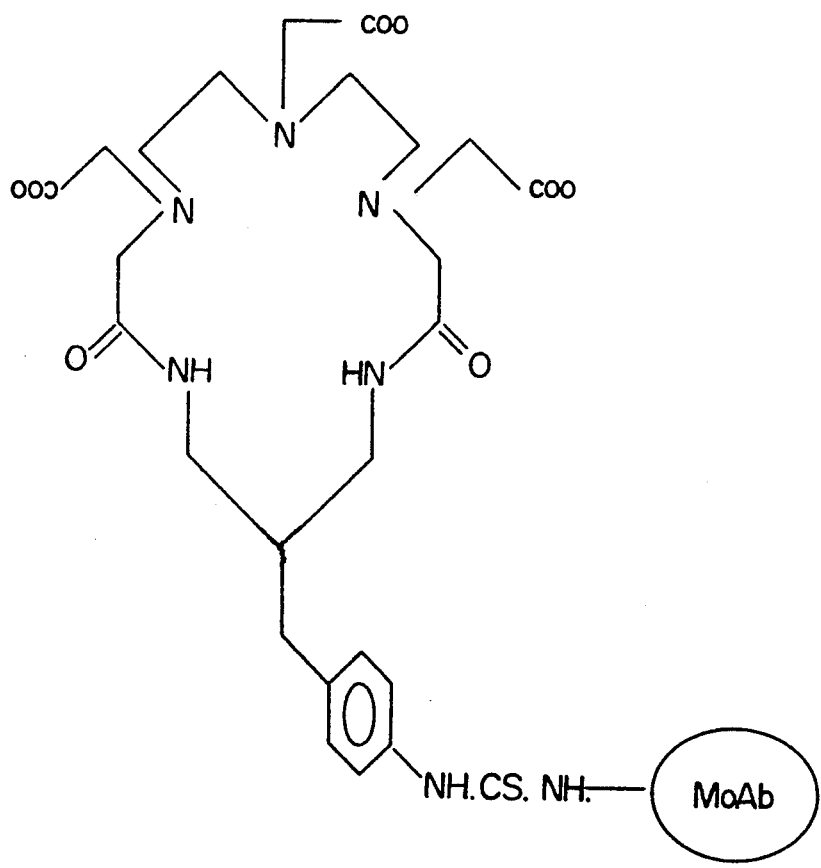
FIG. 12 illustrates HETA-MoAb conjugates.
Figure 13:
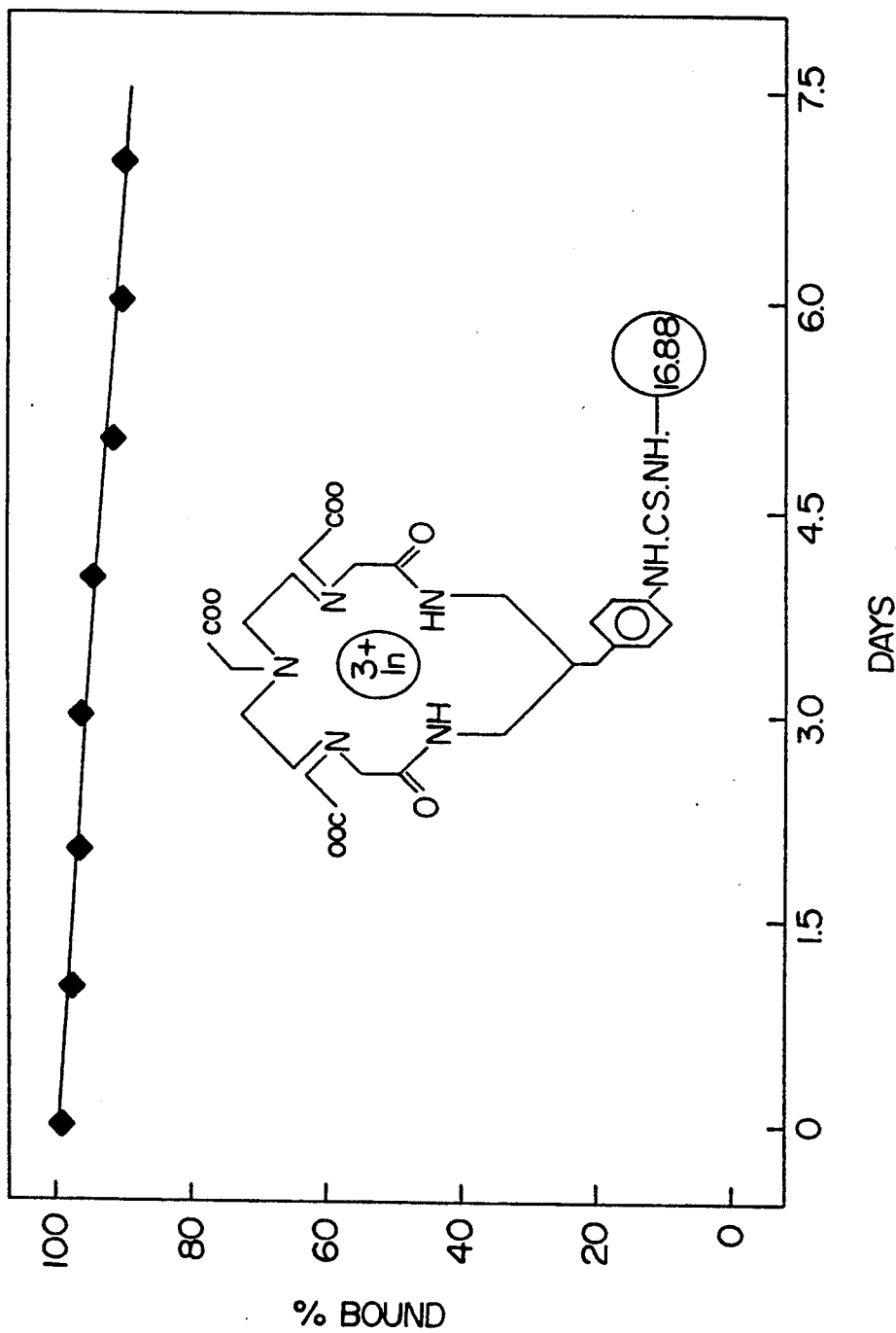
FIG. 13 illustrates the stability of 16.88-HETA.In(111) conjugates.

Under these reaction conditions, DTPA ethyl ester comes off the column first, followed by the cyclic product (HETA) and the LiLo ethyl ester (FIG. 8). These three products have different Rf values in TLC, as shown in FIG. 9. The TLC Rf values of In(111) labeled LiLo, HETA and DTPA chelates are provided for comparison (FIG. 10). The formation of the cyclic product was confirmed by spectral analyses using IR, NMR and FAB MS. The FAB mass spectral data are provided in FIG. 11. Also, when the reaction volume was 500 mL (methylene chloride), the DTPA anhydride coupling to the diamine resulted exclusively in the formation of the cyclic product HETA. The nitro derivative of HETA was converted to isothiocyanate derivative of HETA as follows: 500 mg of nitro-HETA was taken in 50 ml of absolute ethanol and reduced to amine derivative using catalytic amounts of PD/C(10%) under hydrogen atmosphere. The solution was filtered and 1 ml of thiophosgene was added dropwise. The solution was stirred for 2 hours and rotoevaporated to obtain the isothiocyanate derivative of HETA. This product was further purified by silica gel column chromatography using 4% methanol in methylene chloride as the solvent (Yield 350 mg). The isothiocyanate derivative of HETA thus obtained was coupled to the human monoclonal antibody 16.88. The resultant 16.88-HETA conjugate was labeled with In(111), and incubated with excess DTPA to assess stability. Stability of the radioimmunoconjugate was followed over a period of 7 days. The results are shown in FIG. 13. 16.88-HETA.In(111) was much more stable than 16.88-DTPA.In(111).

We claim:

1. A complex comprising a polypeptide bound to the chelating agent HETA of the formula:

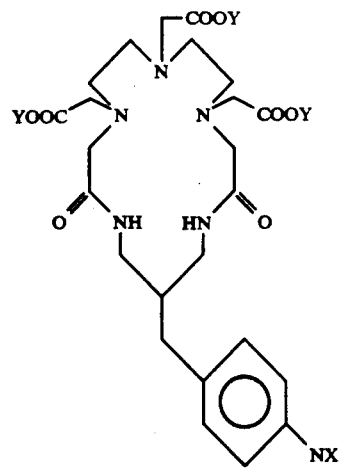

wherein X is selected from the group consisting of $O_2$, NBr, $H_2$, $HCOCH_2Br$ and CS; and Y is selected from the group consisting of H, $CH_3$ and $C_2H_5$.

2. The complex of claim 1, wherein the polypeptide is an antibody.

3. The complex of claim 1, comprising a radionuclide bound to the chelating agent.

4. A complex comprising a polypeptide bound to the chelating agent DICAP:

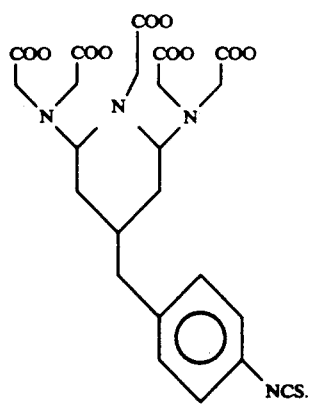

5. The complex of claim 4 comprising a radionuclide bound to the chelating agent DICAP.

6. The complex of claim 4 comprising a metal bound to the chelating agent DICAP.

7. A complex comprising a polypeptide bound to the chelating agent LiLo:

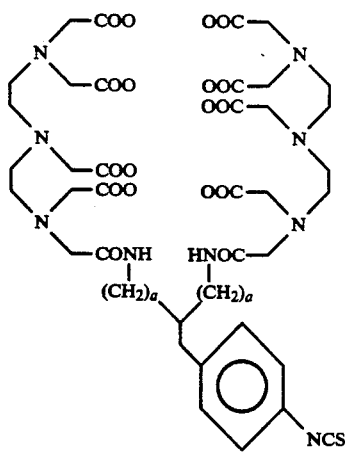

n = 1, "a" LiLo1
n = 2, "b" LiLo2 wherein n is 1 or 2.

8. The complex of claim 7 comprising a radionuclide bound to the chelating agent LiLo.

9. The complex of claim 7 comprising a metal bound to the chelating agent LiLo.

10. A complex comprising a polypeptide bound to the starburst LiLo ligand:

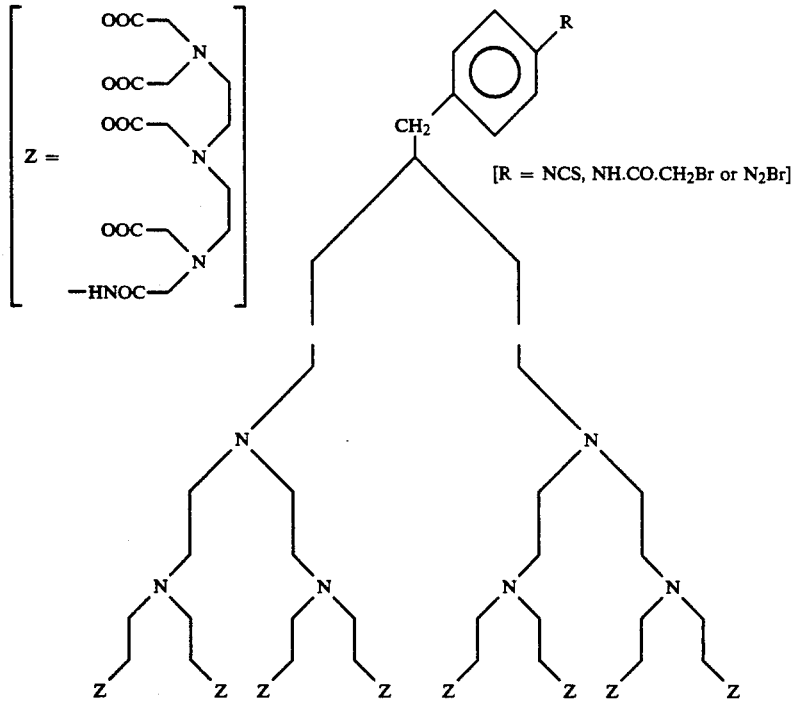

wherein Z is

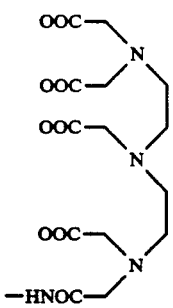

until a desired number of COO binding sites are available in n rows of N, and a number of COO for binding $=2^{n+1}$] and R is NCS, NHCOCH$_2$Br or N$_2$Br.

11. The complex of claim 10 comprising a radionuclide bound to the starburst LiLo ligand chelating agent.

12. The complex of claim 10 comprising a metal bound to the starburst LiLo ligand chelating agent.

13. The complex of claim 10, wherein the polypeptide is an antibody.

14. The complex of claim 1, comprising a metal bound to the chelating agent.

15. The complex of claim 4, wherein the polypeptide is an antibody.

16. The complex of claim 7, wherein the polypeptide is an antibody.

* * * * *

UNITED STATES PATENT AND TRADEMARK OFFICE
CERTIFICATE OF CORRECTION

PATENT NO. : 5,292,868

DATED : March 8, 1994

INVENTOR(S) : Ramaswamy Subramanian and James L. Colony

It is certified that error appears in the above-identified patent and that said Letters Patent is hereby corrected as shown below:

Title page, item [75],

Please add the name -- James L. Colony -- to the "Inventor:"

Signed and Sealed this

Twenty-eighth Day of June, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,292,868
DATED : March 8, 1994
INVENTOR(S) : Ramaswamy Subramanian and James L. Colony It is certified that error appears in the above-identified patent and that said Letters Patent is hereby corrected as shown below:

On the title page, item [75]: insert after first Inventor:
--James L. Colony, Seattle, Wa.--

This certificate supersedes Certificate of Correction issued June 28, 1994.

Signed and Sealed this

Twenty-seventh Day of June, 1995

Attest:

BRUCE LEHMAN

Attesting Officer

Commissioner of Patents and Trademarks